United States Patent [19]

Beentjes et al.

[11] 4,441,701
[45] Apr. 10, 1984

[54] APPARATUS FOR SUPPORTING AND GUIDING A SUB-LANCE

[75] Inventors: Nicolaas H. Beentjes, Uitgeest; Peter Gootjes, Alkmaar, both of Netherlands

[73] Assignee: Estel Hoogovens B.V., Netherlands

[21] Appl. No.: 419,184

[22] Filed: Sep. 17, 1982

[30] Foreign Application Priority Data

Sep. 25, 1981 [NL] Netherlands ............... 8104325

[51] Int. Cl.$^3$ ............................................. C21C 5/46
[52] U.S. Cl. ................................... 266/287; 266/226
[58] Field of Search .............. 266/287, 78, 226, 100, 266/79, 88, 225, 89, 223, 217, 99; 73/304 R, DIG. 9; 294/81 R, 82 R

[56] References Cited

U.S. PATENT DOCUMENTS 3,501,136  3/1970  Schweng et al. ............... 266/226

FOREIGN PATENT DOCUMENTS 41-7922    4/1966  Japan ........................... 266/226
50-138129  7/1975  Japan .
337406     1/1972  U.S.S.R. ...................... 266/226
379631     7/1973  U.S.S.R. ...................... 266/226

Primary Examiner—L. Dewayne Rutledge
Assistant Examiner—S. Kastler
Attorney, Agent, or Firm—Stevens, Davis, Miller & Mosher

[57] ABSTRACT

To support and guide a sub-lance for a metallurgical furnace, a sub-lance carriage 3 and sub-lance guide 4 run on a track 1. The guide 4 is below the carriage and moves in dependence on the carriage movement for part of the carriage travel. To provide a simple means for control of the movement of the guide, the guide is suspended by a support 6, such as a cable, the top end of which engages the carriage but is caught by fixed stops 8 when the carriage moves below a certain point. The cable 6 is housed within a tubular guide 5 over part of its length.

2 Claims, 5 Drawing Figures

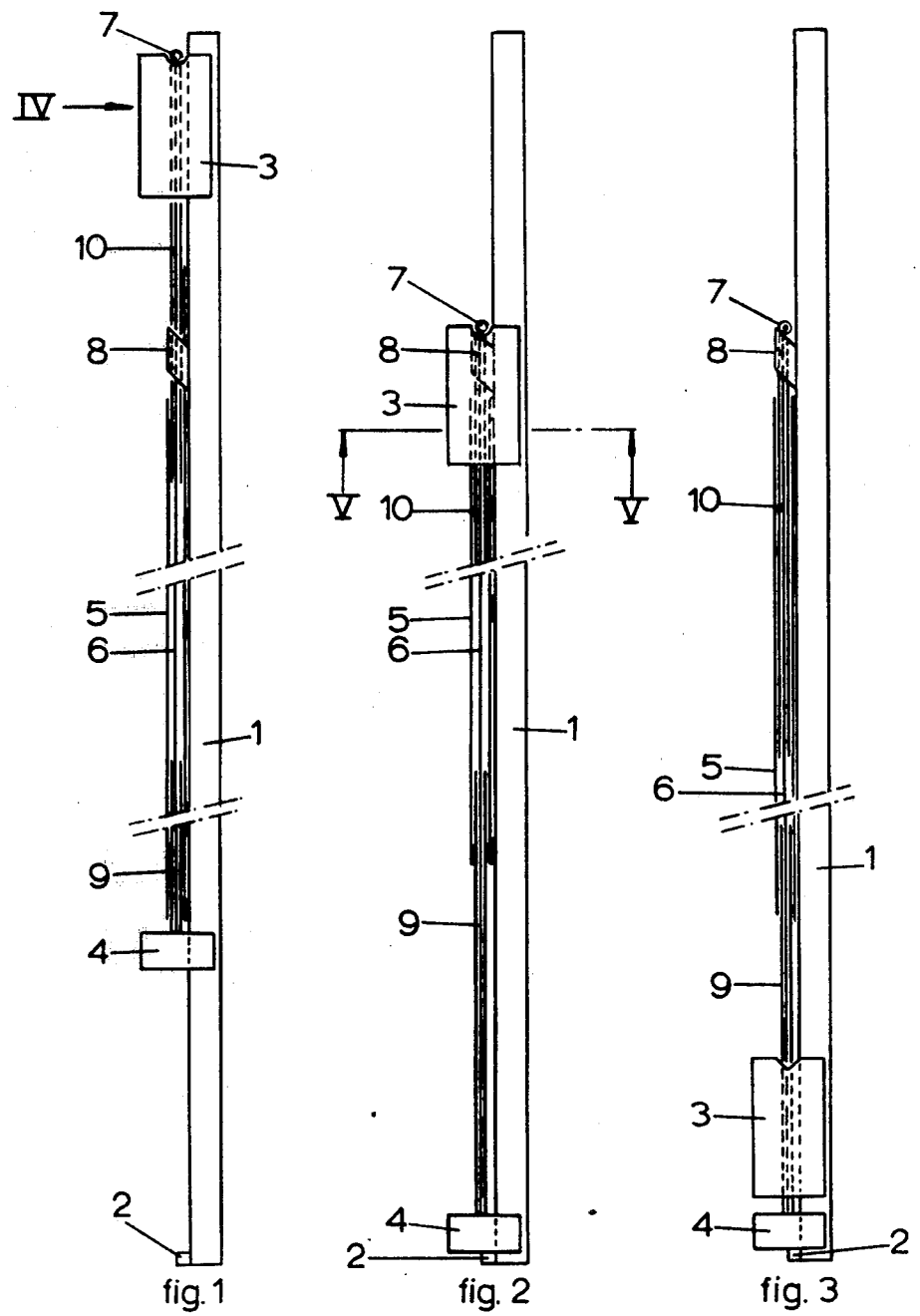

APPARATUS FOR SUPPORTING AND GUIDING A SUB-LANCE

BACKGROUND OF THE INVENTION

1. Field of the Invention

This invention relates to apparatus for supporting and guiding a sub-lance which carries out measurements and/or taking of samples in a steel furnace.

2. Description of the Prior Art

In the preparation of steel in a steel furnace, use is often made of a sub-lance in order to take temperature and/or oxygen measurements during the refining process, and also to take samples on the basis of which the further progress of the process is controlled. For this purpose a water-cooled sub-lance is briefly put into the furnace so that a measurement or sampling probe reaches into the melt. The sub-lance is then removed.

An apparatus for supporting the sub-lance and guiding its movement is disclosed in Japanese laid-open patent application no. 90506/75 (application no. 138129/73 dated Dec. 13, 1973) and comprises a vertical guide track, a sub-lance carriage which moves along this guide track and in which the sub-lance is suspended, and a sub-lance guide which moves along the same guide track below the sub-lance carriage. Connecting means including a supporting cable cause the sub-lance guide to be located in dependence on the position of the sub-lance carriage.

Because of the great length of the sub-lance and the conditions in which it is used, accurate guidance with the aid of a sub-lance guide as described above is important. During the time when the sub-lance is lowered into the furnace, the sub-lance guide should be located as close as possible to the entry point of the sub-lance into the furnace in order to maintain the guidance of the sub-lance. The guide must be raised when the sub-lance is at its highest position, in order to maintain contact with the sub-lance, because when the sub-lance is removed from the furnace, there must be enough room to change the measuring probe, which means that the lance must be removed some distance above the furnace. There is thus the requirement that not only the sub-lance carriage in which the sub-lance is suspended must be movable along the guide track, but the sub-lance guide also must be movable even if over a shorter distance only.

In the Japanese patent publication mentioned above, the sub-lance guide is suspended on a cable and balanced by a counter-weight via a pulley. Special apparatus must be provided in order to ensure that the sub-lance guide and the cable is moved suitably in dependence on the position of the sub-lance or the sub-lance carriage.

SUMMARY OF THE INVENTION

The object of the present invention is to provide a simplified construction of apparatus for guiding and supporting a sub-lance which provides for the movement of the sub-lance guide and the required adjustment to the position of the sub-lance carriage without the use of a counter-weight and/or a special drive system for the sub-lance guide.

The invention is set out in the claims. It consists in an arrangement in which support means for the sub-lance guide engages the sub-lance carriage and moves therewith during the movement of the sub-lance carriage over the upper part of its path. There is a fixed stop means on the guide track by which the said support means is held when the sub-lance carriage is below the above-mentioned upper part of its path. A tubular guide houses the said support means from near the said stop to near the uppermost position of the sub-lance guide.

When the sub-lance carriage descends from its topmost position, the sub-lance guide also descends until the guide support means comes to rest on the stop means. As the sub-lance carriage moves lower, the sub-lance guide remains at this lowest position until the sub-lance carriage returns above the fixed support, when the guide support means is again moved upwardly so that the sub-lance guide is brought up again.

The tubular guide should house the support means (e.g. a cable) over by far the greater part of its extent so that steady movement of the sub-lance guide is obtained, and there is no possibility that the cable will deviate and come into contact with other moving parts. Additional security in this respect can be obtained if tubular covering elements are located at both ends of the guide support means and extend into the tubular guide for all positions of the sub-lance guide. Thus the cable of the support means is enclosed throughout its length. These two tubular covering elements move inside of tubular guide. It is alternatively feasible that the end portions of the support means are in the form of rods which extend into the tubular guide at each position of the sub-lance guide, so that transverse movement of the support means is limited.

The support means for the sub-lance guide preferably is at least partly a cable, but alternatively it is possible to make use of a cord or chain. One attraction of using a cable lies in its elasticity. If the sub-lance guide at its lowest position is supported by a stop, then as the sub-lance guide is moved downwards and meets this stop at its lowest position, the elasticity of the cable ensures a reduction of the shock with which the sub-lance guide meets the stop. Conversely when the support means is picked up by the sub-lance carriage from its stop means the shock is reduced.

Although separate stop means may be provided for the support of the sub-lance guide support means, it is alternatively possible to use for these stop means the upper end of the tubular guide.

It will be clear that the inventive principle described above is applicable irrespective of the particular construction of the sub-lance, the sub-lance carriage and the sub-lance guide. It is also not of importance what type of steel furnace is involved, or what type of suction hood above the furnace. In addition also the invention is described above in relation to a steel furnace, it may be applied to other kinds of metallurgical furnace to which a sub-lance is fitted.

BRIEF INTRODUCTION OF THE DRAWINGS

The preferred embodiment of the invention will now be described by way of non-limitative example with reference to the accompanying drawings, in which:

FIG. 1 is a diagrammatic view of sub-lance guide and support apparatus embodying the invention, showing the topmost position of the sub-lance carriage.

FIG. 2 shows the same apparatus with the sub-lance carriage at a lower position at which the sub-lance guide comes to a stop in its downward movement.

FIG. 3 shows the same apparatus with the sub-lance carriage and the sub-lance guide both in their lowest positions.

DESCRIPTION OF THE PREFERRED EMBODIMENT

Figure 4:
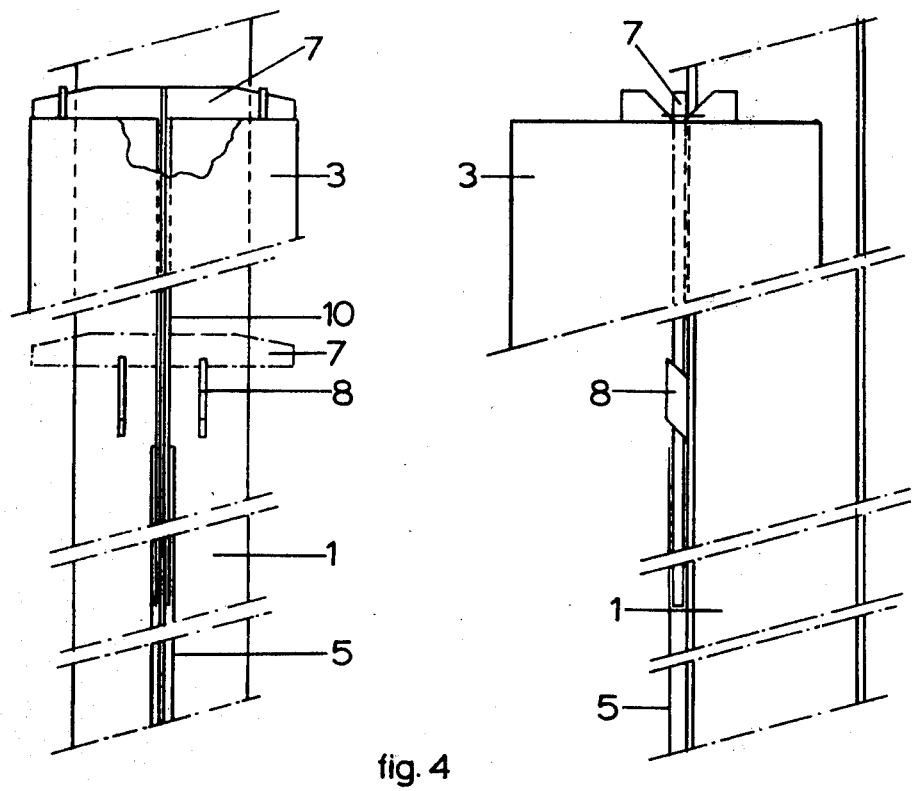
FIG. 4 is a view on an enlarged scale of part of FIG. 1 (right hand part of FIG. 4) and a front of the same part in the direction of arrow IV of FIG. 1 (left part of FIG. 4).

FIGS. 1, 2 and 3 show a carriage guide track 1 with a bottom stop 2. The track 1 has an H-profile (see FIG. 5) and along it moves a sub-lance carriage 3 and a sub-lance guide 4. In use, the whole apparatus is located above a furnace and the sub-lance is suspended from the carriage 3 and guided by the guide 4. Both the sub-lance carriage 3 and the sub-lance guide 4 are guided along the flanges or the body of the H-profile on wheels, in accordance with a well-known arrangement which is not relevant to the principles of this invention and need not therefore be described in detail.

A tubular cable guide 5 is fastened to the guide track 1 along a substantial portion of its length, and a cable 6 extends through this cable guide 5 and has its lower end fastened to the sub-lance guide 4. This cable 6 constitutes a support element for the sub-lance guide 4. At its upper end the cable 6 is fastened to a cross-bar 7 which is able to rest in a notch in the upper side of the sub-lance carriage 3. Just above the upper end of the cable guide 5 there is a fixed stop 8 fastened to the guide track 1. The cross-piece 7 is caught by this stop 8 when the sub-lance carriage 3 is moved past the stop 8 in a downward direction.

Figure 5:
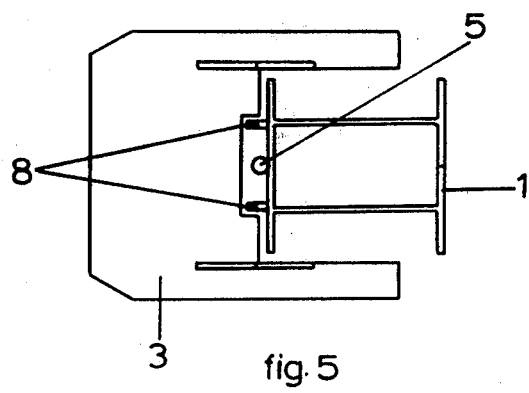
FIG. 5 is a schematic cross-section on the line V—V of FIG. 2.

It can be seen from FIG. 5 that there is a gap between the sub-lance carriage 3 and the front face of the guide track 1. This gap allows the carriage to move without hindrance along the cable guide 5 and past the fixed support 8. FIG. 5 also shows how the sub-lance carriage 3 extends along the sides of the guide track 1. Guide rollers or wheels on the carriage run along the guide track at the sides thereof (not shown, as mentioned above).

A tube 9 is fastened to the sub-lance guide 4, and extends along the cable 6, with which it moves. The tube 9 extends into and fits loosely in the cable guide 5. Likewise there is a tube 10 fastened to the cross-piece 7 and extending along the cable 6 into the cable guide 5 in which it fits loosely. The length of the tubes 9 and 10 is such that they both reach into the cable guide 5 at every position of the sub-lance guide. The tubes 9 and 10 form covering elements for the cable 6 and maintain its position when slack.

FIG. 1 shows the sub-lance carriage 3 in its highest position, with the sub-lance guide 4 also in its highest position. Here the sub-lance guide 4 is supported by the cable 6, and the cross-piece 7 rests in the notch on the upper face of the carriage 3.

FIG. 2 shows the situation during downward movement of the sub-lance carriage 3 when the sub-lance guide 4 meets the stop 2. On further downward displacement of the sub-lance carriage 3 the tension in the cable 6 decreases and its elastic extension disappears. After this has happened, the cross-piece 7 comes to rest on the fixed stop 8 when the cable 6 is quite slack. However, in this position the cable 6 is supported in the lateral direction over its whole length by the tubes 9 and 10 and the cable guide 5.

FIG. 3 shows the sub-lance carriage descended yet further into its lowest position, in which it comes to rest on the sub-lance guide 4. The drive means for the sub-lance carriage 3 is not shown, not affecting the principle of this invention but in conventional manner is achieved by means of a cable which is driven by a suitable power system located above the upper end of the guide track 1.

FIG. 4 shows in more detail how the cross-piece 7 rests in the notch in the upper face of the sub-lance carriage 3, and that the fixed stop means 4 consists of two hooks, one on each side of the cable guide 5.

What is claimed is:

1. Apparatus for supporting and guiding a sub-lance which carries out measurements and/or taking of samples in a metallurgical furnace, said apparatus having
   (a) a guide track,
   (b) a sub-lance carriage to support the sub-lance and displaceable upwardly and downwardly along said guide track while being guided by the track,
   (c) a sub-lance guide displaceable upwardly and downwardly along said guide track below the sub-lance carriage while being guided by the track,
   (d) support means for the sub-lance guide consisting at least partly of an elongate flexible support element for the sub-lance guide, and being connected to said sub-lance carriage so as to move therewith over an upper portion of the travel of the carriage, whereby the sub-lance guide moves in dependence on the movement of the carriage said support means having, at its upper end, a cross-bar which rests upon the sub-lance carriage during movement of the latter over the said upper portion of its travel and which is caught by said stop means when the sub-lance carriage moves below said upper portion of its travel, said flexible support element of said support means extending from the upper end of the support means to the sub-lance guide, and the support means including two tubular covering elements surrounding said flexible support element and extending respectively from the upper end thereof and from the sub-lance guide into the said tubular guide so that the lengths of the support element outside the tubular guide are enclosed by said covering elements at all positions of the sub-lance guide,
   (e) stop means to hold said support means, located in a fixed position relative to said guide track, so that, on movement of the carriage below said upper portion of its travel, the support means is held by stop means, and
   (f) a tubular guide housing said support means over at least part of the distance from said stop means to the upper end of the travel of the sub-lance guide.

2. Apparatus for supporting and guiding a sub-lance which carries out measurements and/or taking of samples in a metallurgical furnace, said apparatus having
   (a) a guide track,
   (b) a sub-lance carriage to support the sub-lance and displaceable upwardly and downwardly along said guide track while being guided by the track,
   (c) a sub-lance guide displaceable upwardly and downwardly along said guide track below the sub-lance carriage while being guided by the track,
   (d) support means for the sub-lance guide consisting at least partly of an elongate flexible support element for the sub-lance guide, and being connected to said sub-lance carriage so as to move therewith over an upper portion of the travel of the carriage, whereby the sub-lance guide moves in dependence on the movement of the carriage said support means having, at its upper end, a cross-bar which rests upon the sub-lance carriage during movement of the latter over the said upper portion of its travel and which is caught by said stop means when the sub-lance carriage moves below said upper portion of its travel, wherein the upper and lower end portions of the support means are provided by respective rods which each are of sufficient length to extend into said tubular guide at all positions of the sub-lance guide, (e) stop means to hold said support means, located in a fixed position relative to said guide track, so that, on movement of the carriage below said upper portion of its travel, the support means is held by stop means, and (f) a tubular guide housing said support means over at least part of the distance from said stop means to the upper end of the travel of the sub-lance guide.

* * * * *